United States Patent [19]

Peterson et al.

[11] Patent Number: 5,429,673
[45] Date of Patent: Jul. 4, 1995

[54] BINARY VAPOR ADHESION PROMOTERS AND METHODS OF USING THE SAME

[75] Inventors: William R. Peterson, Phoenix, Ariz.; Craig M. Stauffer, Sunnyvale, Calif.

[73] Assignee: Silicon Resources, Inc., Phoenix, Ariz.

[21] Appl. No.: 130,620

[22] Filed: Oct. 1, 1993

[51] Int. Cl.$^6$ .............................................. C09D 5/00
[52] U.S. Cl. ................................. 106/287.11; 106/285
[58] Field of Search ........................... 106/285, 287.11

[56] References Cited

U.S. PATENT DOCUMENTS 3,549,368 12/1970 Collins et al. ........................ 96/35.1
5,116,715 5/1992 Roland et al. ........................ 430/190

*Primary Examiner*—David Brunsman
*Attorney, Agent, or Firm*—Panitch Schwarze Jacobs & Nadel

[57] ABSTRACT

Novel compositions are provided for use in the vapor priming of substrates used in the preparation and production of microelectronic devices comprising a first component comprising an organosilane having a hydrolyzable silicon-nitrogen bond and a second component selected from the group consisting of a second organosilane different from the first component having a hydrolyzable silicon-nitrogen bond, a hydrocarbon, an ether, a disiloxane and an alkoxysilane in which all components have substantially the same boiling points at atmospheric pressure. These compositions which are vaporized and transported to an area of silylation on a substrate by an inert gas, silylate the substrate surface and provide for uniform successful coating with organic films. These organosilane mixtures allow for rapid vapor priming and silylation steps in the manufacture of microelectronic devices with successful subsequent coating of the substrates with uniform organic films.

11 Claims, No Drawings

BINARY VAPOR ADHESION PROMOTERS AND METHODS OF USING THE SAME

Field of the Invention

This invention is directed to two-component compositions useful for treating semiconductor wafers by vapor priming methods.

BACKGROUND OF THE INVENTION

Microelectronic devices have become ubiquitous in our society and touch all aspects of our lives. They are the driving force for many technologies. Within the past two decades, the manufacture of microelectronic devices has burgeoned into a multibillion dollar business. This business is specifically concerned with the various types of microelectronic devices available, referred to as chips. Developments in past years have increased the performance and design of these devices from initial introductory models which contained only a few thousand transistors per chip to current models which contain millions of transistors per chip in approximately the same area. The increased performance requirements and the higher density of transistors on these chips have caused greater demand for improvements on current manufacturing methods.

Early methods for preparation of devices consisted of use of photolithographic techniques wherein a photoresist was placed or coated on a substrate, usually silicon, imaged with light and developed into desired patterns with suitable developers. The resulting image was then used as a selective mask in subsequent operations such as ion implanting, patterning of the underlying substrate, metal plating or various other required steps for the production of microelectronic devices. These earlier photoresist applications presented a number of problems including poor photoresist coating of the substrate wafer, lifting-off of photoresist patterns from devices, and subsequent pattern loss due to portions of photoresist being carried off by developer when the developer undercut the resist. Undercutting is a deleterious process wherein an aqueous or organic developer migrates along the surface of a polar substrate and causes a photoresist to lose its adhesive ability.

Hexamethyldisilazane (HMDS) was found to be a significant solution to many of these problems. As a pretreatment to a photoresist application, HMDS when applied to substrates was found to promote better photoresist coating on the substrates, reduce undercutting and prevent photoresist film lift-off during development. The noticeable improvement in coating properties is the result of the reaction of HMDS with water molecules, hydrogen bonded to the substrate surface, and the subsequent reaction of HMDS with hydroxide and oxide groups present on the surface. The HMDS reaction with the water molecules produces ammonia and trimethylsilanol. The subsequent reaction with the hydroxyl and oxide groups produces a trimethylsiloxy substituted surface. Incorporating trimethylsilyl groups on the surface reduces surface energy and provides a monomolecular organic coating which is compatible with organic photoresists. The hydrophobic trimethylsilyl groups repel polar groups such as water and aqueous developers, preventing undercutting at the substrate-photoresist interface. HMDS was rapidly employed by all device manufacturers due to its delivery of an increase in yield.

Further improvements to the early priming techniques, which comprised applying liquid HMDS or HMDS diluted in various solvents, developed in subsequent years through the application of HMDS in a vapor form. The methods comprised placing the substrate in an oven at a reduced pressure and treating the substrate with HMDS vapor. These methods gave more consistent coverage and were more efficient regarding reaction time and required materials. Today, vapor priming of wafers is a method of choice in the manufacture of these high density devices.

Vapor priming, while superior to liquid priming, requires more time for the actual priming operation. Recent methods of vapor priming include utilizing state-of-the-art, in-line track priming in which a substrate wafer is placed on a track and transported to an area where heat and vacuum are applied. A device covers the wafer, and a vacuum is applied as heat is supplied to the substrate. HMDS vapor is introduced into the area surrounding the wafer when the proper vacuum is achieved. The vacuum is broken and the wafer is transported to the next operation. A successful vapor priming step enables acceptable photoresist films, or other organic-based films, to be applied in subsequent steps. An acceptable photoresist film is a continuous, uniform film that does not exhibit pin-holes, edge pull-back, beading, lifting and/or significant undercutting during development.

A measurement of the degree of surface silylation achieved during vapor priming is effectively quantified by the surface contact angle as measured by a goniometer. Higher degrees of silylation cause a reduced surface energy resulting in higher contact angles for a water bead placed upon a surface. A contact angle in the range of from about 65° to 75° is suitable for good coating characteristics in most applications. For some substrates, however, it is desirable to reach a higher degree of silylation for good coating characteristics as indicated by contact angles of up to 80°. The contact angle measurements are significant in that they provide proof of the level of silylation that is obtained with the various techniques described. The higher the contact angle, the more silylation has taken place. Therefore, a high contact angle indicates a greater number of trimethylsilyl groups bonded to the substrate surface.

Typical in-line vapor track priming of a wafer using HMDS may require in excess of two minutes in order to obtain sufficient surface silylation and to allow for successful photoresist coating. The subsequent process in the track, photoresist coating, typically requires about one minute or less. Therefore, a significant portion of the time required to produce the finished device is consumed in the vapor priming operation. The priming step may limit otherwise faster operations. A high density device may use up to 20 to 25 masking steps or levels, each of which requires prior photoresist application for the HMDS priming. Attempts to decrease this priming time by increasing substrate temperatures, increasing the amount of HMDS vapor, and changing pressure have been ineffectual in reducing the amount of time for priming.

Other silylation agents are known which could impart the trimethylsilyl moiety to the substrate surface. Notable among them is trimethylsilyldiethylamine (TMSDEA). This compound is known to rapidly and completely silylate substrate surfaces at low temperatures. However, the material is so reactive that control of the extent of surface silylation is not easily achieved with over-silylation a frequent occurrence. The over-silylation of the surface promotes the wetting of a photoresist and a blistering or "blowoff" of the photoresist during imaging. The latter is caused by a high degree of silylation which acts as a release agent with nitrogen gas evolved during exposure, lifting off sections or pieces of the photoresist film.

SUMMARY OF THE INVENTION

According to the present invention, it has been discovered that certain organosilane mixtures, wherein the components have substantially the same boiling points when applied in vapor form, silylate as a single compound, providing excellent and rapid surface vapor priming with a high degree of reproducibility.

The compositions of the present invention comprise a mixture of two components which have substantially the same boiling points at atmospheric pressure. The first organosilane component comprises an organosilane which has a hydrolyzable silicon-nitrogen bond. The second component is selected from the group consisting of an organosilane which is different than the first component and has a hydrolyzable silicon-nitrogen bond, a hydrocarbon, an ether, a disiloxane, or an alkoxysilane.

It has been discovered that such organosilane mixtures silylate surfaces at controllable rates. However, silylation occurs more rapidly than expected from the ratio of the components. The unexpected increase in both the silylation coverage and the speed of the coverage is not predictable from the compositions. The degree of silylation and the degree of coverage remain constant and controllable without significant change as the compositions are applied in vapor form.

DETAILED DESCRIPTION OF THE PREFERRED EMBODIMENT

Vapor priming systems as used herein comprise any device or hardware such as an oven, a vapor prime oven, in-line vapor prime track equipment or any other device utilized to expose a wafer or similar microelectronic substrate to organosilane vapor at pressures equal to or below atmospheric pressure in order to cause a chemical reaction (silylation) at or on the surface of the substrate to enable subsequent coating with a uniform organic film. The compositions herein described can be utilized with any of the above mentioned types of equipment.

Silanes utilized in the instant compositions are hydrolyzable liquid organosilanes having within the molecular structure at least one silicon-nitrogen bond. Such organosilanes remain in the liquid phase until transported to an area where silylation is to occur. The organosilane can be transported in the vapor form by an inert gas such as nitrogen or argon, injecting it into a low pressure silylation area through an orifice, in liquid or vapor form, or mechanically spraying it into a heated area where the vapor is transported by an inert gas or by vacuum to a silylation area. Generally the liquid organosilanes used in accordance with the instant invention are described as being silicon-substituted monomers containing at least one hydrolyzable group bound to silicon. The hydrolyzable group bound to silicon is a nitrogen species with the nitrogen being bound to the silicon.

Suitable organosilanes which remain in the liquid phase but volatilize to the vapor phase at reduced pressures and which have sufficient solubility in inert gases, such as nitrogen or argon, include hexamethyldisilazane (HMDS), trimethylsilyldimethylamine (TMSDMA), and trimethylsilyldiethylamine (TMSDEA) having the following structures:

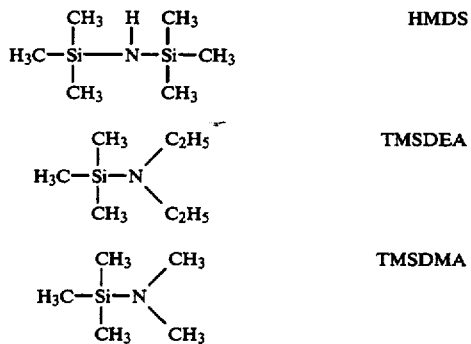

The liquid silanes used in this invention have substantially the same boiling points when employed in a mixture. Preferably the silanes employed include at least a binary mixture of a silazane, such as HMDS, and a dialkylamino silane, such as TMSDEA or TMSDMA. In general, the organosilane(s) of the present compositions can be diluted with other inert materials such as hydrocarbon solvents, ethers and other silane derivatives such as disiloxanes and alkoxysilanes having substantially the same boiling points as the organosilanes with which they are mixed. Preferably, the boiling points of the components of these compositions deviate from one another by no greater than about 5° C., more preferably no greater than about 1° C. or about 2° C.

These compositions may be provided in a wide range of concentrations and mixture ratios depending upon the equipment within which the mixture is to be used, the temperature at which silylation is to occur, and the substrate to be treated. Suitable organosilanes which remain substantially in the liquid phase, are soluble in gases and other silanes and solvents, and are able to be vaporized by vacuum, with or without additional heat. In addition, suitable organosilanes should function in the vapor phase to provide silylation of various substrate surfaces include silanes and mixtures of silanes having a trimethylsilyl group bound to a saturated or unsaturated monoalkylamine, a saturated or unsaturated dialkylamine in which the alkyl groups are the same or different or a saturated or unsaturated cycloalkylamine or heterocyclicamine group. These organosilanes may be represented by the following general formula:

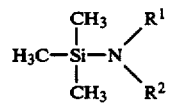

wherein $R^1$ selected from a group consisting of hydrogen, saturated alkyl and unsaturated alkyl group, $R^2$ is selected from the group consisting of saturated alkyl and unsaturated alkyl which may be the same or different from $R^1$, saturated and unsaturated cycloalkyl, and saturated and unsaturated cycloalkyl with heteroatoms, or $R^1$ and $R^2$ may form a saturated or unsaturated cycloalkyl or heterocyclic group with the nitrogen atom.

Examples of suitable compounds include n,n-trimethylsilyldiisopropylamine, t-trimethylsilyldiethylamine, trimethylsilyldimethylamine, t-butylaminotrimethylsilane, trimethylsilylpiperdine, trimethylsilylacetamide, n-trimethylsilylallylamine, n-trimethylsilylimidazole, trimethylsilylmorpholine, 3-trimethylsilyl-2-oxazolidinone, trimethylsilylpyrazole, trimethylsilylpyrrolidine, 2-trimethylsilyl-1,1,2,3-triazole, and 1-trimethylsilyl-1,2,4-triazole.

Suitable silazanes which remain substantially in the liquid phase, are soluble with gases and other silanes and solvents and which function in the vapor phase to provide silylation of various substrate surfaces include disilazanes of the formula:

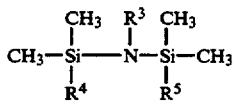

wherein $R^3$ is hydrogen, methyl, trimethylsilyl or dimethylsilyl and $R^4$ and $R^5$ are independently selected from the group consisting of hydrogen, methyl, alkyl and vinyl, or cyclodisilazanes of the formula:

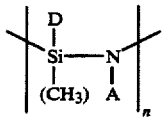

wherein n is 3 or 4; D is selected from the group consisting of methyl, hydrogen and vinyl; and A is selected from the group consisting of hydrogen and methyl. Suitable disilazanes and cyclodisilazanes include hexamethyldisilazane, n-methylhexamethyldisilazane, 1,3-di-n-octyltetramethyldisilazane, 1,3-divinyltetramethyldisilazane, heptamethyldisilazane, nonamethyltrisilazane, tris(dimethylsilyl)amine, 1,1,3,3,5,5-hexamethylcyclotrisilazane, 1,2,3,4,5,6-hexamethylcyclotrisilazane, octamethylcyclotetrasilazane, and 1,3,5-trimethyl-1,3,5-trivinylcyclotrisilazane.

Suitable organic solvents for use in these compositions selected from the class of aliphatic and aromatic hydrocarbons and aliphatic ethers which have substantially the same boiling points as the organosilanes with which they are mixed include preferably hydrocarbons such as n-octane or toluene, and aliphatic ethers such as methoxyethylether.

Preferably the composition is comprised of a ratio of a first suitable organosilane component which comprises at least one hydrolyzable silicon-nitrogen bond to a second mixture component selected from the group consisting of an organosilane, different from that of the first component and having at least one single hydrolyzable silicon-nitrogen bond, a hydrocarbon, an ether, a disiloxane, and an alkoxysilane of from about 0.1:99.9 to 99.9:0.1, with both components in the mixture having substantially the same boiling points at atmospheric pressure. Preferably, the mixture comprises the components, HMDS and TMSDEA in concentrations in a ratio of from about 0.1:99.9 to 99.9:0.1 TMSDEA to HMDS, the preferred component ratio being 99:1 HMDS to TMSDEA.

Preferred mixtures of a single organosilane with either a hydrocarbon or an ether include a mixture of TMSDEA and n-octane in a ratio of from about 0.1:99.9 to 99.9:0.1 TMSDEA to n-octane, or a mixture of trimethylsilylpiperdine and methoxyethylether in a ratio of from about 0.1:99.9 to 99.9:0.1 trimethylsilylpiperdine to methoxyethylether.

These mixture are introduced into vapor priming equipment such as a GENESIS 2020 vapor prime unit, a GENESIS 2010 vapor prime unit, a GENESIS 2002 vapor prime oven, an in-line vapor track system or any other type of vapor priming equipment. The vaporized mixtures are transported by an inert gas, such as nitrogen or argon within the vapor priming equipment or by differential pressure flow to the area of silylation on the surface of a substrate within the vapor priming equipment. Silylation preferably occurs at a temperature of from about 25° C. to about 200° C. After silylation, a coating of a uniform organic film is provided to the substrate. Examples of such films include photoresist, polyimide, silicon polyimide, and other uniform organic surfaces.

The compositions have significant advantages over use of the separate component materials individually, the most significant being that separate tracks or containers, including bubblers, and other application hardware are not required for difficult to prime substrates. Traditionally, substrates that are difficult to vapor prime with HMDS have to be transported to and treated in other equipment, or treated with more active materials such as trimethylsilyldiethylamine. The present compositions, however, can be used in existing hardware currently employing HMDS without modification.

This invention enables controllable vapor priming and surface silylation using reactive silylation materials, such as trimethylsilyldiethylamine, which if used alone, would typically over-silylate a substrate surface even at ambient temperatures, thus rendering the surface unusable due to lack of photoresist adhesion and/or loss of pattern or of photoresist during imaging due to nitrogen evolution. It has been discovered that the rate of silylation is greater than expected based on component ratio and that the rate of substrate priming is more rapid at ambient temperatures and above ambient temperatures than would normally be expected.

The present compositions solve problems in the art such as overpriming and underpriming and allows for controllable, reproducible priming in present equipment with little modification in a shorter period of time with increased materials economics. The compositions of the invention are useful for all systems utilizing organosilane vapor to treat microelectronic substrates to allow subsequent coating of the substrates with uniform organic polymer film such as, for example, photoresist, polyimide, and silicon polyimide.

In sum, the invention overcomes the above noted deficiencies of the prior art by providing superior, more rapid, controllable vapor priming of microelectronic substrates, and providing compositions suitable for in-line vapor priming track applications which permit broad process latitude by enabling reproducible substrate vapor priming at a wide range of temperatures. Moreover, the invention provides compositions of materials which vapor prime a substrate more economically and more rapidly than its components taken separately, and promote silylation of a variety of different substrates suitable for a successful subsequent photoresist coating in the same equipment with the same binary silane compositions, as well as providing varying amounts of surface silylation suitable for subsequent photoresist application depending upon the vapor contact time with the substrate. The invention will now be described in more detail with reference to the following specific, non-limiting examples:

EXAMPLE 1

A composition was formed consisting of 95 parts HMDS and 5 parts TMSDEA. The mixture was utilized to treat silicon wafers in a GENESIS 2020 vapor prime unit at a pressure of 5–400 torr measured by a capacitance manometer or a convection type vacuum gauge. The dehydration bake cycle of the unit was not employed and silylation of the silicon substrates began when temperature equilibrium was achieved. A goniometer was used to measure the contact angles of the treated wafers. After one minute of exposure to the vapor mixture, a contact angle of 75° was measured. Under identical conditions, substrates treated with only HMDS had a 47° contact angle, and substrates treated with only TMSDEA had an 84° contact angle.

EXAMPLE 2

A composition of 99 parts HMDS and 1 part TMSDEA was prepared and utilized to treat bare silicon wafers in a GENESIS 2020 vapor prime unit at a constant temperature of 50° C. Treatment times of 20, 40 and 60 seconds were used. Measured contact angles at these treatment times were 68°, 71° and 73°, respectively. Under identical conditions, HMDS only required 15 minutes to achieve a contact angle of 68°.

EXAMPLE 3

Bare silicon wafers which exhibit typical contact angles of less than 15° were treated with a composition of 99 parts HMDS and one part TMSDEA. The compositions were introduced into a GENESIS 2020 vapor prime oven operating at 60° C. The wafers were treated in the oven for 30 seconds. The composition was used to prime the wafers with the same vacuum conditions described in Example 1 above. The average contact angle measured for 100 treated bare silicon wafers ranged from initial measurements of 70° to final contact angle measurements of at 72°, with an overall average of 71°.

EXAMPLE 4

A composition of 99 parts HMDS and 1 part TMSDEA was utilized to treat silicon wafers having a silicon nitride substrate previously cleaned in an oxygen plasma. After plasma treatment, the substrates exhibited an approximate contact angle of 15° Vapor treatment with this composition at a temperature of 50° C. for 30 seconds resulted in a measured contact angle of 79°. Under identical conditions for only 10 seconds, a contact angle of 76° was obtained.

EXAMPLE 5

A silicon wafer was pretreated such that a surface of silicon dioxide having a measured contact angle of less than 15° was provided for this example. The wafer was treated for 10 seconds in a vapor prime unit with a composition consisting of 85 parts n-octane (boiling point=125°–127° C.) and 15 parts TMSDEA at a temperature of 100° C. The contact angle measured for the treated substrate was 78°. Identical conditions using HMDS only for silylation showed a measured contact angle of 45°. The wafers treated with the n-octane/TMSDEA composition were then coated with positive photoresist by standard coating practices of spinning with subsequent soft-bake for solvent removal. The photoresist coated wafer exhibited a uniform coating with no edge pull back and satisfactory imaging.

EXAMPLE 6

Bare silicon wafers were treated with a composition of 10 parts trimethylsilylpiperdine and 90 parts methoxyethylether in a GENESIS 2020 vapor prime unit fitted with a HOT-BLOCK® adaptor and a temperature of 100° C. The oven was maintained at 110° C. and vapor contact time was 30 seconds. The measured contact angle of the silylated wafers was found to 81°.

EXAMPLE 7

Bare silicon wafers were treated with a composition of 98 parts HMDS and 2 parts TMSDEA, on an in-line track system at 500 torr nitrogen flowing at a rate of 6 liters/min at 50° C. with a vapor contact time of 15 seconds before venting to the atmosphere. Measured contact angles for the vapor were 10 71° . The wafer was successfully coated with photoresist and imaged.

EXAMPLE 8

A variety of substrates consisting of polysilicon, silicon dioxide (thermal), silicon dioxide (CVD), and BPSG boron phosphate spun-on glass were treated with a composition of 99.5 parts HMDS and 0.5 parts TMSDEA under vapor prime conditions of 60° C. and a 30 second contact time. Measured contact angles indicated acceptable silylation for all substrate surfaces.

The novel compositions of this invention are expected to be useful for a wide range of compositions and mixtures to improve vapor priming of substrates for the manufacture of microellectronic devices. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A composition for vapor treatment of substrates comprising a mixture of:
   (a) a first component comprising an organosilane having a hydrolyzable silicon-nitrogen bond; and
   (b) a second component selected from the group consisting of an organosilane different from said first component and having a hydrolyzable silicon-nitrogen bond, a hydrocarbon, an ether, a disiloxane, or an alkoxysilane, wherein said first and second components have substantially the same boiling points at atmospheric pressure.

2. A composition according to claim 1 wherein said boiling points are no greater than about 5° C. apart.

3. A composition according to claim 1, wherein the first component comprises an organosilane of the formula:

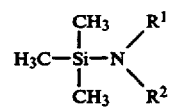

wherein $R^1$ is selected from the group consisting of hydrogen, saturated alkyl and unsaturated alkyl, $R^2$ is selected from the group consisting of saturated alkyl and unsaturated alkyl which may be the same or different from $R^1$, saturated and unsaturated cycloalkyl, and saturated and unsaturated cycloalkyl with heteroatoms, or R¹ and R² may form a saturated or unsaturated cycloalkyl or heterocyclic group with the nitrogen atom.

4. A composition according to claim 1, wherein the second component comprises an organosilane of the formula:

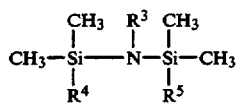

wherein $R^3$ is hydrogen, methyl, trimethylsilyl or dimethylsilyl and $R^4$ and $R^5$ are independently selected from the group consisting of hydrogen, methyl, alkyl and vinyl.

5. A composition according to claim 1, wherein the second component comprises a cycloorganosilane of the formula:

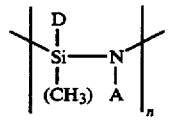

wherein n is 3 or 4; D is selected from the group consisting of methyl, hydrogen and vinyl; and A is selected from the group consisting of hydrogen and methyl.

6. The composition according to claim 1 wherein the components are present in the mixture in a ratio of the first component to the second component of from about 0.1:99.9 to 99.9:0.1.

7. The composition according to claim 1 wherein said first component is trimethylsilyldiethylamine, and said second component is hexamethyldisilazane.

8. The composition according to claim 7 wherein the ratio of hexamethyldisilazane to trimethylsilyldiethylamine is 99:1.

9. The composition according to claim 1 wherein said second component is selected from the group consisting of n-octane, toluene and methoxyethylether.

10. The composition according to claim 9 comprising at least 1 part trimethylsilyldiethylamine and no greater than 399 parts n-octane.

11. The composition as in claim 9 comprising at least 1 part trimethylsilylpiperdine and no greater than 99 parts methoxyethylether.

* * * * *